United States Patent [19]

Sramek

[11] Patent Number: 5,551,435

[45] Date of Patent: Sep. 3, 1996

[54] METHOD AND SYSTEM FOR MANAGING HEMODYNAMIC STATE AND OXYGEN TRANSPORT

[76] Inventor: Bohumir Sramek, 19211 Edgehill Dr., Irvine, Calif. 92715

[21] Appl. No.: 452,271

[22] Filed: May 26, 1995

[51] Int. Cl.$^6$ ..................................................... A61B 5/00

[52] U.S. Cl. ........................ 128/668; 128/672; 128/687; 128/691; 128/713

[58] Field of Search .................................. 128/668, 672, 128/677, 680–3, 691–694, 713, 734; 604/50, 65–67

[56] References Cited

U.S. PATENT DOCUMENTS

| | | | |
|---|---|---|---|
| 5,002,055 | 3/1991 | Merki et al. ............................... | 604/66 |
| 5,054,493 | 10/1991 | Cohn et al. ............................... | 128/672 |
| 5,103,828 | 4/1992 | Sramek ...................................... | 128/668 |
| 5,269,301 | 12/1993 | Cohen ......................................... | 604/66 |

FOREIGN PATENT DOCUMENTS 9000367  1/1990  WIPO ..................................... 128/713

OTHER PUBLICATIONS

Hurst, W. J. *The Heart*– McGraw–Hill, 1982. p. 93.
Shoemaker, W. C. et al. "Hemodynamics and Oxygen Transport Responses in Survivors and Nonsurvivors of High–Risk Surgery." *Critical Care Medicine*, vol. 21, No. 7, p. 977, 1993.

*Primary Examiner*—Angela D. Sykes
*Assistant Examiner*—Robert L. Nasser, Jr.
*Attorney, Agent, or Firm*—David A. Farah; Sheldon & Mak, Inc.

[57] ABSTRACT

A method of attaining a preselected systemic hemodynamic state in an patient using a per-beat basis, such as for example paired values of MAP and SI, rather than a per-minute basis, such as MAP and CI. A method of utilizing Hemodynamic Management Charts (HMCs) which permits the integration of data concerning systemic hemodynamic modulators and the systemic hemodynamic state, and which allows the identification of deviations in the levels of the hemodynamic modulators from normal levels. Also, a computer-based system which measures hemodynamic parameters and implements at least one HMC into its software, thereby permitting identification of deviations in the levels of hemodynamic modulators from normal levels. Therapeutic corrections of the deviations in hemodynamic modulator levels, such as through pharmacologically active agents or volume expanders, based on the foundation and HMCs enables the clinician to establish and maintain a patient in the normal hemodynamic state and normal perfusion state.

13 Claims, 4 Drawing Sheets

FIG. 1 HEMODYNAMIC MANAGEMENT CHART FOR RESTING SUPINE ADULTS

Figure 2:
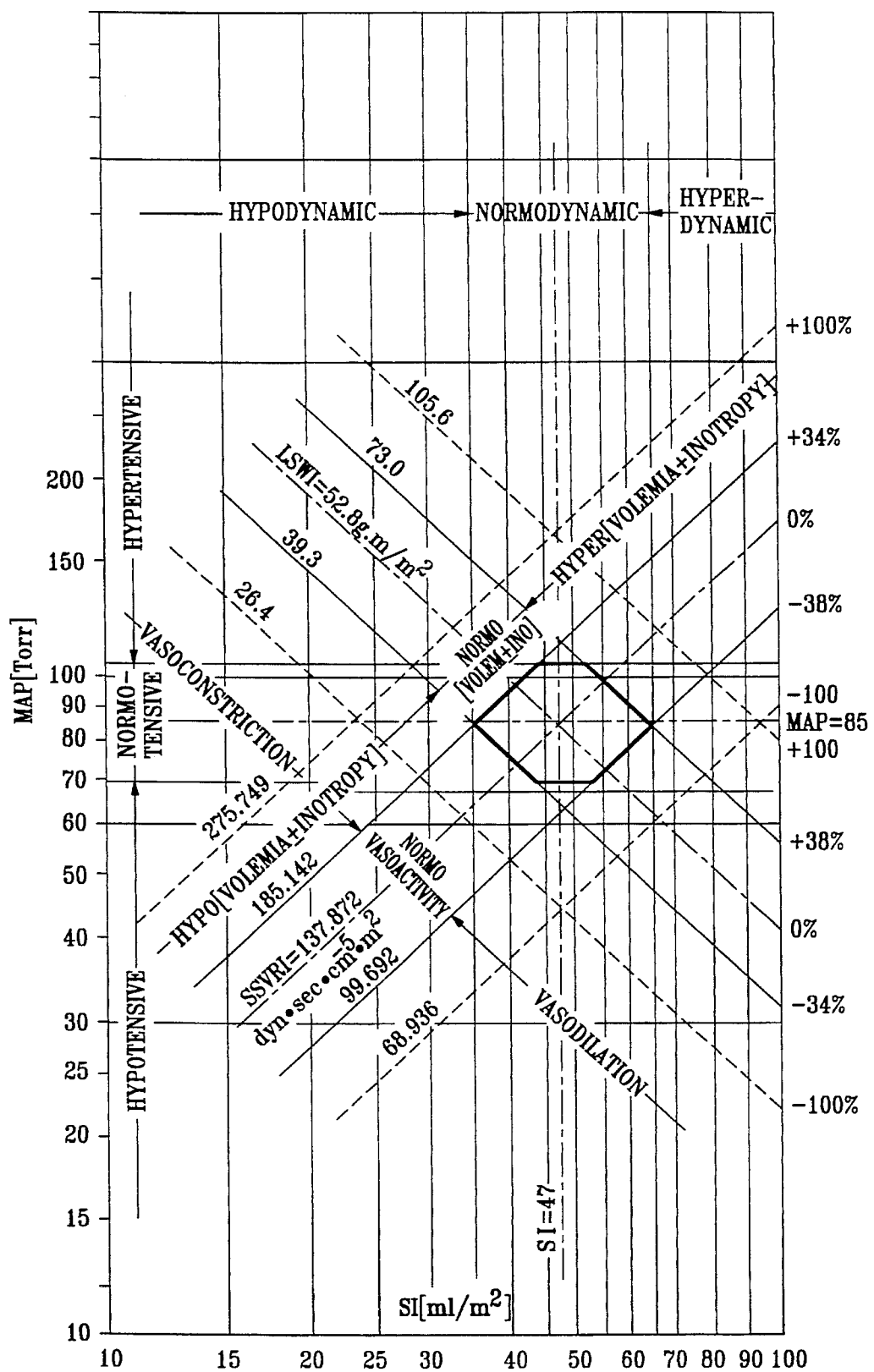

Fig. 2 HEMODYNAMIC MANAGEMENT CHART FOR RESTING SUPINE ADULTS

METHOD AND SYSTEM FOR MANAGING HEMODYNAMIC STATE AND OXYGEN TRANSPORT

NOTICE OF INCLUSION OF COPYRIGHTED MATERIAL

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND

The systemic hemodynamic state of a mammal is defined by the relationship between blood pressure and global blood flow at the output node of the left heart. The normal hemodynamic state can be altered as a result of conditions such as congestive heart failure and essential hypertension, and secondary to trauma and surgery.

Blood pressure and global blood flow are determined in turn by several interrelated systemic hemodynamic modulators. These modulators include intravascular volume (volemia), inotropy, vasoactivity and chronotropy.

In general, blood pressure is used as the major indicator of systemic hemodynamic state because blood pressure has been measured easily and non-invasively for many decades using sphygmomanometry and because physicians have been trained to rely on it. However, using blood pressure as the major indicator of systemic hemodynamic state can lead to incomplete and inaccurate diagnoses and to inappropriate therapeutic measures.

The primary function of the cardiovascular system in mammals is the transport of oxygen. Oxygen transport is related to global blood flow (stroke index and cardiac index), like the systemic hemodynamic state but, unlike the systemic hemodynamic state, is not related to blood pressure.

Measurement of global blood flow to determine a patient's oxygen transport or hemodynamic state can be made either invasively by the thermodilution method or noninvasively using Thoracic Electrical Bioimpedance. Unfortunately, the availability of methods of monitoring global blood flow has not changed the hemodynamic and oxygen transport management of patients. There are several reasons for this failure. First, physicians still tend to rely solely on blood pressure measurements to make diagnoses and to make therapeutic decisions concerning a patient's hemodynamic state and oxygen transport. Second, medical education has not absorbed recent advances in the noninvasive measurement of global blood flow. Therefore, physicians graduate without a clear understanding of the role that global blood flow measurements can have in diagnosis and treatment of defects in oxygen transport. Lacking this understanding, physicians incorrectly target symptoms such as hypertension or a low flow state for therapeutic intervention rather than identifying and therapeutically correcting abnormal levels in the systemic hemodynamic modulators which are the underlying causes.

Further, current cardiovascular care is primarily reactive to catastrophic events rather than preventive. This approach has led to substantial failures in diagnosis and treatment. For example, it is estimated that death is the first indication of a cardiovascular disorder in 40% of persons.

Therefore, it would be advantageous to have a method of diagnosing and treating cardiovascular disorders based on an understanding of the relationship between the systemic hemodynamic state and systemic hemodynamic modulators. Further, it would be advantageous to have a method utilizing information on global blood flow to determine and treat specific causes of cardiovascular disorders. Also, it would be useful to have an automated system utilizing these methods.

SUMMARY

The present invention is directed to a method of attaining a preselected combination of MAP and SI in an patient. The method comprises the steps of first determining the patient's mean arterial pressure (MAP) and stroke index (SI). Next is determined the patient's deviation from ideal of hemodynamic modulators intravascular volume, inotropy, and vasoactivity using the MAP and SI determined in the first step. Then, a desired combination of MAP and SI is preselected and therapeutic doses of one or more pharmacologically active agents or volume expanders for altering one or more of the hemodynamic modulators are administered to attain the preselected combination of MAP and SI.

The present invention is also directed to a method of attaining a preselected combination of MAP and SI in an patient. The method comprises the steps, first, of determining the patient's mean arterial pressure and stroke index. Next, a desired combination of MAP and SI is preselected. Then, therapeutic doses of one or more pharmacologically active agents or volume expanders for altering the patient's MAP or the patient's SI is administered to attain the preselected combination of MAP and SI.

The present invention is further directed to a method of attaining a preselected combination of MAP and SI, or a preselected combination of LSWI and SSVRI in an patient. The method comprises the steps of first determining the patient's mean arterial pressure (MAP), stroke index (SI), left stroke work index (LSWI) and stroke systemic vascular resistance index (SSVRI). Next is determined the patient's deviation of the combined hemodynamic modulators [volume±inotropy], $d[V\pm I]$, from normovolemia/normoinotropy, the patient's Inotropic State Index (ISI) to determine the deviation from normoinotropy, the patient's deviation in volemia, $dV$, from normovolemia, and the patient's deviation in vasoactivity, $d(Vaso)$, from normovasoactivity. Then, a desired combination of MAP and SI, or a desired combination of LSWI and SSVRI is preselected. Next, therapeutic doses of one or more pharmacologically active agents or volume expanders for altering one or more hemodynamic modulators are administered to attain the preselected combination.

In each method, the patient can be one or more of the following: a neonate, a child, an adult male, a non-pregnant women of child bearing age, a pregnant women, an elderly man and an elderly women. Further, the one or more pharmacologically active agents or volume expanders can be selected from the group consisting of a positive inotrope, a negative inotrope, a vasoconstrictor, a vasodilator, a diuretic, a positive chronotrope and a negative chronotrope. Also, in adults, the preselected combination of MAP and SI can be a MAP between about 70–105 Torr and an SI between about 35–65 ml/m$^2$. The preselected combination of LSWI and SSVRI can be a LSWI between about 39.3–73.0 g.m/m$^2$ and an SSVRI between about 99,692–185,142 dyn.sec.cm$^{-5}$.m$^2$.

FIGURES

Figure 1:
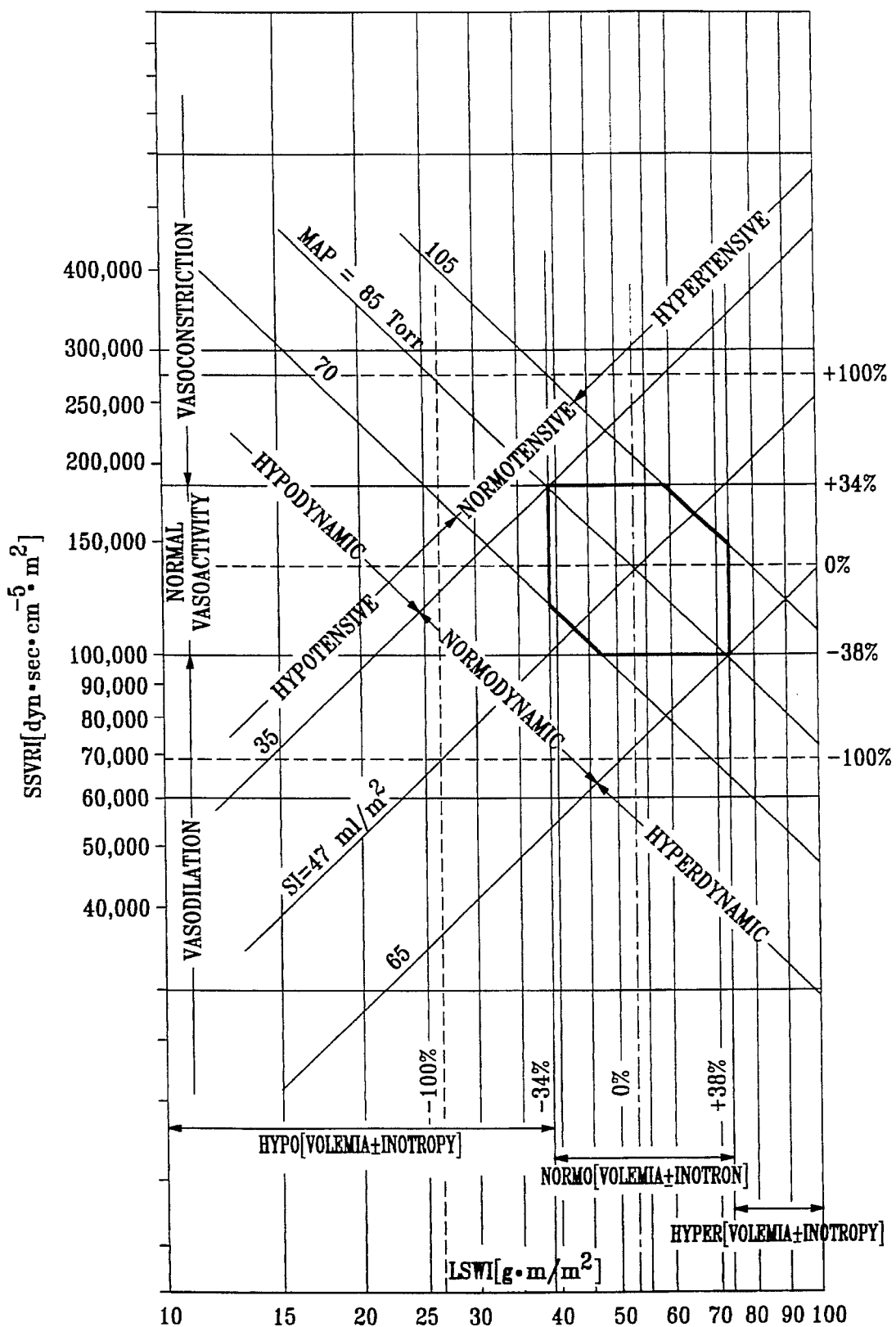

The features, aspects and advantages of the present invention will become better understood with regard to the following description, appended claims and accompanying figures where:

FIG. 1 resents a Hemodynamic Management Chart plotted on log/log graph paper in which hemodynamic modulators LSWI and SSVRI form the orthogonal system of coordinates and the resulting systemic hemodynamic state, MAP and SI, are the parameters.

FIG. 2 presents a Hemodynamic Management Chart plotted on log/log graph paper in which MAP and SI form the orthogonal system of coordinates and systemic hemodynamic modulators LSWI and SSVRI are the parameters.

Figure 3:
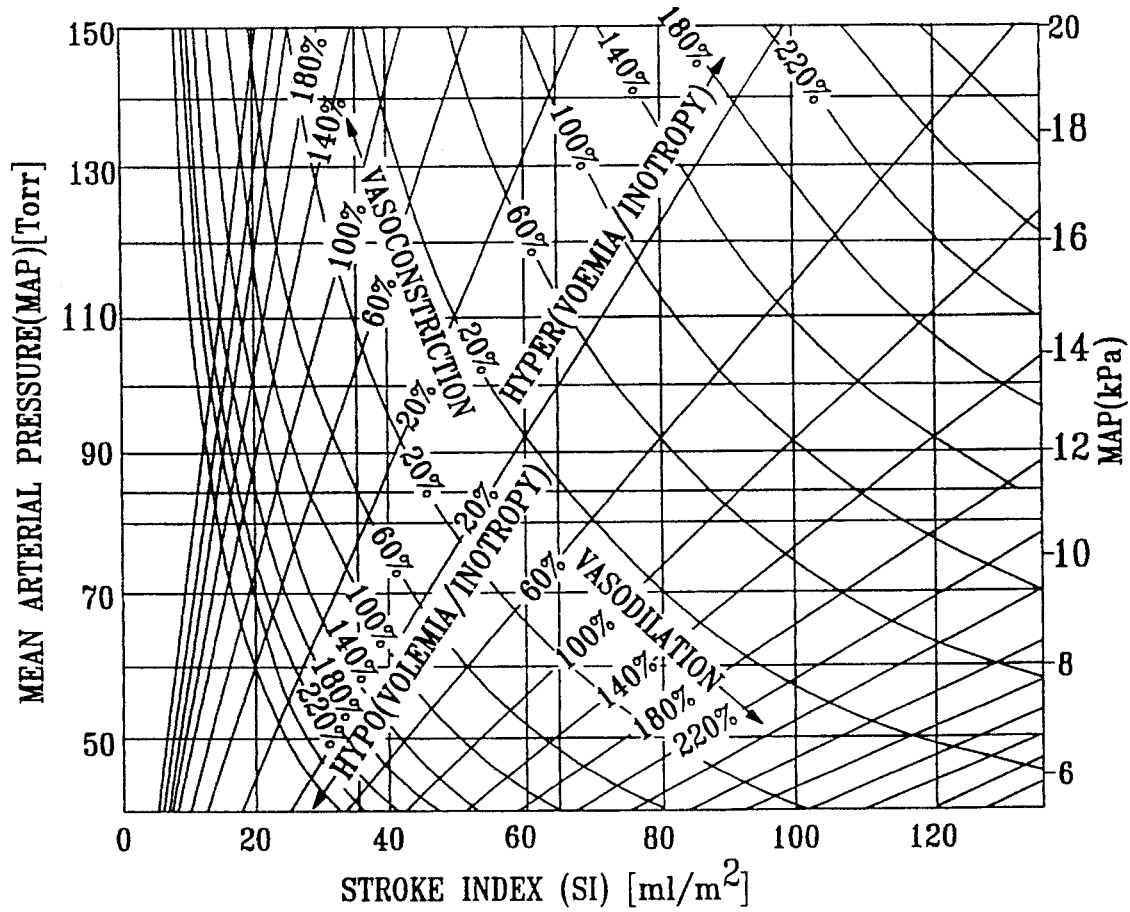

FIG. 3 presents a Hemodynamic Management Chart plotted on linear scale graph paper in which MAP and SI form the orthogonal system of coordinates and systemic hemodynamic modulators LSWI and SSVRI are the parameters.

Figure 4:
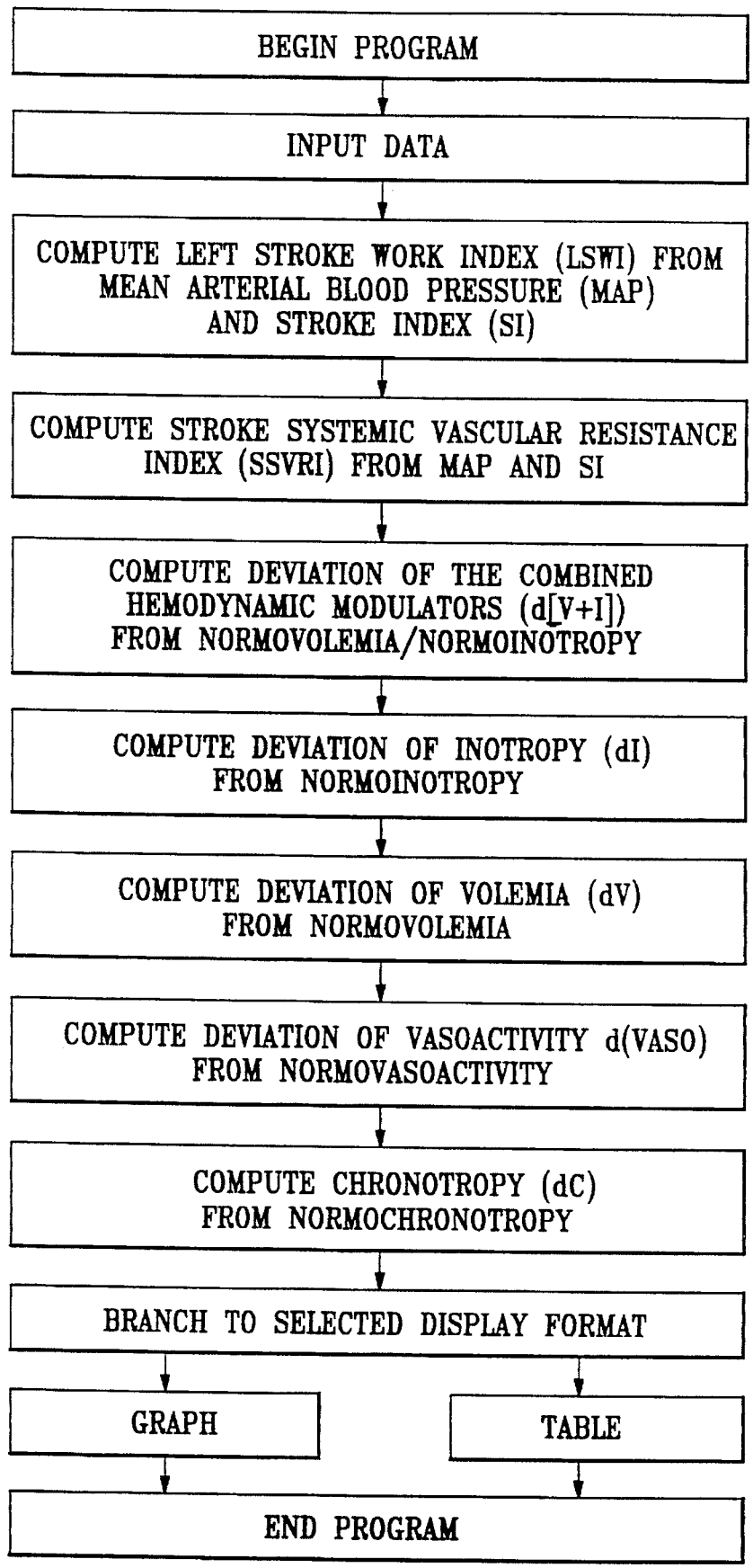

FIG. 4 a flow chart of a computer program algorithm for implementing one version of the present invention.

DESCRIPTION

According to one embodiment of the present invention, there is provided a method of attaining a preselected hemodynamic state in an patient using a physiologic foundation for understanding the normal and abnormal systemic hemodynamic state disclosed herein. The foundation employs a per-beat basis, using for example paired values of MAP and SI, rather than a conventional per-minute basis, using for example MAP and CI.

The present invention further provides a Hemodynamic Management Chart (HMC) which permits the integration of data concerning systemic hemodynamic modulators and the systemic hemodynamic state, and allows the identification of deviations in the levels of the hemodynamic modulators from normal levels. The present invention also includes a computer-based system which measures hemodynamic parameters and implements at least one HMC into its software, thereby permitting identification of deviations in the levels of hemodynamic modulators from normal levels. Therapeutic corrections of the deviations in hemodynamic modulators, such as through pharmacologically active agents or volume expanders, based on the foundation and HMCs disclosed herein enables the clinician to establish and maintain the patient in the normal hemodynamic state. The goal of this approach is to change the objective of cardiovascular health care from the reactive (response to catastrophic events) to proactive (maintenance of health).

RELATIONSHIPS BETWEEN THE SYSTEMIC HEMODYNAMIC STATE, OXYGEN TRANSPORT AND THE SYSTEMIC HEMODYNAMIC MODULATORS

The systemic hemodynamic state of a mammal is defined by the relationship between blood pressure and blood flow at the output node of the left heart. There are a number of cardiovascularly-significant quantities whose relationships must be understood to appreciate the invention disclosed herein.

The hemodynamically-significant measure of blood pressure is the Mean Arterial Pressure (MAP) [Torr, mmHg]. The hemodynamically-significant measure of blood flow is the Stroke Index (SI) [ml/m$^2$]. The perfusion-significant measure of blood flow is the Cardiac Index (CI) [l/min/m$^2$]. Cardiac Index is related to Stroke Index and Heart Rate (HR) [beats/min] as follows:

$$CI = (SI \times HR)/1000 \qquad (1)$$

where the constant 1000 is used to convert milliliters into liters.

The Global Oxygen Delivery Index (DO$_2$I) [ml/min/m$^2$], is related to CI as follows:

$$DO_2I = CI \times Hgb \times SaO_2 \times 1.34 \times 10 \qquad (2)$$

where Hgb is hemoglobin [g/dl], SaO$_2$ [%] is the percentage saturation of O$_2$ in arterial blood and the constant 1.34 is the hemoglobin affinity and the constant 10 converts deciliters to liters. In a nonhemorrhaging patient with a normal lung function, Hgb and SaO$_2$ in Eq.2 are constants. Therefore, for most patients and clinical states, changes in CI reflect equivalent changes in DO$_2$I.

The most important oxygen transport parameter is the global Oxygen Consumption Index, VO$_2$I [ml/min/m$^2$]. VO$_2$I can be determined if the saturation of oxygen in the mixed venous blood, SvO$_2$ [%], is known utilizing the formula:

$$VO_2I = CI \times Hgb \times (SaO_2 - SvO_2) \times 1.34 \times 10 \qquad (3)$$

The cardiovascular system adjusts the systemic hemodynamic state for every heart beat to satisfy varying metabolic demand and to respond to different physiologic stimuli. Though both blood pressure and blood flow change essentially continually, their mean values over one heart beat interval are clinically adequate measures of the systemic hemodynamic state. Therefore, the dynamic response of the cardiovascular system to continuously varying metabolic demands is provided by dynamic variation of CI.

CI (and therefore DO$_2$I) can increase 300–400% in normal individuals and can increase up to 500% in an athletic individual at peak physical exercise. This increase occurs through a three-fold increase in HR (for example, an increase from 60 beats/min to 180 beats/min) and a two-thirds increase in SI. See Eq.1. SI and HR increase through a complex regulatory system of systemic hemodynamic modulators. These regulators include intravascular volume, inotropy, vasoactivity and chronotropy.

The MAP, however, is maintained relatively constant even when the hemodynamic modulators change CI and SI in response to increased metabolic demands. This is physiologically necessary to maintain adequate perfusion of the brain and heart because flow to these organs is proportional to the MAP.

DO$_2$I, Eq.2, directly correlates with the quality and duration of life and with increased-survival rates of the surgical and critically-ill patients. Most people achieve an adequate DO$_2$I with normal levels of SI, CI and MAP.

Therefore, utilizing the relationships disclosed above, it can be seen that normal oxygen transport, DO$_2$I and VO$_2$I, is established through normal levels of the systemic hemodynamic modulators, that is normovolemia, normoinotropy, normovasoactivity, and normochronotropy as follows. Normal levels of the hemodynamic modulators produce MAP within the normotensive range and SI within the normodynamic range and, thereby, produce the normal systemic hemodynamic state. Normodynamic SI combined with normochronotropic HR produce normal perfusion blood flow CI (Eq.1). Normal CI, combined with normal Hgb and SaO$_2$, produce normal DO$_2$I (Eq.2). Normal tissue O$_2$ extraction combined with normal DO$_2$I produce normal VO$_2$I (Eq.3).

IDEAL-VALUES AND NORMAL RANGES FOR HEMODYNAMIC PARAMETERS

The systemic hemodynamic state of a patient can be divided into nine categories based on three levels of MAP (hypotension, normotension and hypertension) and three levels of SI (hypodynamic, normodynamic and hyperdynamic state/beat). Only one of the nine categories, simultaneous normotension with a normodynamic state, is the desired systemic hemodynamic state. This normotension/normodynamic systemic hemodynamic state is the hemodynamic component of the therapeutic goal.

Similarly, the perfusion blood flow (CI) can be divided into three categories based on a normal level of SI and three levels of HR (hypochronotropy, normochronotropy and hyperchronotropy). Of these three categories, only a simultaneous normodynamic state and normochronotropy is the desired perfusion blood flow (CI). This normodynamic state/normochronotropy perfusion blood flow is the perfusion component of the therapeutic goal.

Each of the eight abnormal hemodynamic states and the two abnormal perfusion blood flow states result from various combinations of abnormal levels of the hemodynamic modulators, which include intravascular volume (hypovolemia, hypervolemia), inotropy (hypoinotropy, hyperinotropy), vasoactivity (vasodilation, vasoconstriction) and chronotropy (hypochronotropy, hyperchronotropy). However, one or more of the hemodynamic modulators can be normal even though the systemic hemodynamic state or perfusion blood flow state is abnormal.

The normal hemodynamic state varies between individuals and in the same individual under a resting condition as compared to a stressed condition. Parameters for two normal hemodynamic states have been documented. First, the systemic hemodynamic state of resting, supine adults was described in Hurst, W. J. THE HEART. McGraw-Hill, 1982. p.93, incorporated herein by reference in its entirety. The results are summarized in Table I. Second, the hemodynamic and perfusion state for the surgical patients in the immediate postoperative period (1–36 hours) was described in Shoemaker, W. C. et al. "Hemodynamics and Oxygen Transport Responses in Survivors and Nonsurvivors of High-risk Surgery." *Critical Care Medicine*, vol.21, no.7, p.977, 1993, incorporated herein by reference in its entirety.

TABLE I

| Parameter | Ideal mean value | Normal range | Unit |
|---|---|---|---|
| MAP | 85 | 70–105 | Torr (mm Hg) |
| SI | 47 | 35–65 | ml/m$^2$ |
| CI | 3.4 | 2.8–4.2 | l/min/m$^2$ |
| CVP | 4 | −1 to +8 | Torr |
| PAOP | 9 | 6–15 | Torr |
| LAP | 7 | 4–13 | Torr |
| SaO$_2$ | 98 | 94–100 | % |
| Hgb men | 15 | 13–17 | g/dl |
| women | 14 | 12–16 | g/dl |
| LSWI* | 52.8 | 39.3–73.0 | g · m/m$^2$ |
| SVRI* | 1,930 | | dyn · sec · cm$^{-5}$ · m$^2$ |
| SSVRI* | 137,872 | 99,692–185,142 | dyn · sec · cm$^{-5}$ · m$^2$ |
| TEB: | 1.1 | 0.7–1.5 | sec$^{-2}$ |
| ISI men | | | |
| women | 1.3 | 0.9–1.7 | sec$^{-2}$ |

*calculated for ideal values
PAOP = Pulmonary Artery Occluded Pressure (Wedge Pressure)
LAP = Left Atrial Pressure (LAP = PAOP − 2 Torr)
LSWI = Left Stroke Work Index
SSVRI = Stroke Systemic Vascular Resistance index
ISI = TEB-measured Inotropic State Index While the present invention is disclosed specifically with reference to resting supine adults, it will be understood by those with skill in the art with reference to the disclosure herein that the invention can be utilized for the hemodynamic and oxygen transport management of other groups by generating data similar to Table I for each subgroup. These subgroups include surgical patients in the immediate postoperative period, women in child bearing age and in different stages of pregnancy, neonatal and pediatric patients, geriatric patients, hypertensive patients, dialysis patients and patients during physical exercise, among others.

DETERMINING DEVIATIONS OF SYSTEMIC HEMODYNAMIC MODULATOR LEVELS FROM IDEAL LEVELS

The systemic hemodynamic state, defined as paired values of SI and MAP produced at the output node of left heart for each heart beat, is the vectorial result of interaction between myocardial contractile forces and systemic vascular resistance forces taking place during each mechanical systole. The contractile forces produce shortening of myocardial fibers at a rate of contraction which is termed contractility. Modulation of contractility is a sum of mechanical and pharmacologic factors.

The mechanical factor is related to the kinetic forces imparted to the myocardial fibers during diastole (preload) by venous return. The greater the stretch, up to a maximum, the higher the force generated during systole and, thus, the higher the contractility (Frank-Starling Law). Therefore, the modulator of the mechanical embodiment of contractility is intravascular volume.

The pharmacologic factor is related to the presence of certain pharmacological agents (inotropes) which are chemicals that affect the rate of shortening of myocardial fibers. "Positive inotropes" increase contractility while "negative inotropes" decrease contractility.

Systemic vascular resistance forces taking place during ejection phase are the forces of the vasculature which the left ventricle has to overcome to deliver a bolus of blood (SI) into the systemic vasculature during each heart beat. Systemic vascular resistance (vasoactivity) is generally equivalent to the afterload, except in patients with significant changes in blood viscosity. Therefore, the terms "systemic vascular resistance" and "afterload" will be used interchangeably herein. Afterload is affected by the caliber of the vessels of arterial system. The primary modulator of afterload is vasoactivity. Vasodilation decreases afterload, while vasoconstriction increases afterload.

Determining the Left Stroke Work Index

The mean value (integral) of mechanical energy expenditure by the myocardium over a single heart beat interval is the Left Stoke Work Index (LSWI) [g.m/m$^2$]. The LSWI is a product of blood volume expelled by the heart over one heart beat (SI) and blood pressure contribution of the heart (MAP—LAP) according to the following formula:

$$LSWI = SI \times (MAP - LAP) \times 0.0144 \qquad (4)$$

The ideal value for LSWI is 52.8 g.m/m$^2$. See Table I. (PAOP is a clinically acceptable substitute for LAP.)

Determining the Deviations of Actual Volemia and Actual Inotropy from Normovolemia and Normoinotropy Systole is divided into an isovolemic phase and an ejection phase. Contractility of the myocardial fibers during the isovolemic phase is dependent on the inotropic state of the heart but is substantially independent of both preload and afterload. Contractility during the ejection phase is dependent on both volemia (the Frank-Starling mechanism) and the inotropic state.

The magnitude of LSWI corresponds to myocardial oxygen consumption, which takes place only during systole. In addition, the majority of myocardial oxygen is consumed during the isovolemic phase. LSWI is therefore proportional to the magnitude of contractile forces during the combined isovolumic phase and ejection phase Of systole. Thus, LSWI can be used to directly assess of the effects of the hemodynamic modulators volemia and inotropy on contractility during both phases of systole. The relative contribution from each modulator, however, can not be determined from the magnitude of LSWI alone. The ideal value for LSWI given in Table I, 52.8 g.m/m$^2$, corresponds to one of the combinations of normovolemia/normoinotropy, hypovolemia/hyperinotropy and hypervolemia/hypoinotropy.

In order to determine volemia and inotropy, the actual LSWI for a patient is first determined according to Eq.4. The percentage deviation of the combined hemodynamic modulators [volume±inotropy] from normovolemia/normoinotropy, represented by $d[V \pm I]$, can be determined using the actual LSWI and the ideal LSWI (such as from table I). When $LSWI_{actual} > LSWI_{ideal}$, $d[V \pm I]$ is calculated from the formula:

$$d[V \pm I] = +(LSWI_{actual}/LSWI_{ideal} - 1) \times 100 \qquad (5)$$

The sign of the deviation is positive and the prefix of $d[V \pm I]$ is "hyper". The deviation is, thus, expressed as XX% hyper[volemia±inotropy].

When $LSWI_{actual} < LSWI_{ideal}$, the percentage deviation in $d[V \pm I]$ is calculated from the formula:

$$d[V \pm I] = -(LSWI_{ideal}/LSWI_{actual} - 1) \times 100 \qquad (6)$$

The sign of the deviation is negative and the prefix of $d[V \pm I]$ is "hypo". The deviation is, thus, expressed as XX% hypo[volemia±inotropy].

The inotropic state alone, that is separate from the combined effect of volemia and inotropy (LSWI), can be measured from peak aortic blood flow acceleration. TEB measures peak aortic blood flow acceleration non-invasively as the Inotropic State Index, (ISI), [1/sec/sec=sec$^{-2}$] (in older TEB literature called the Acceleration Index, ACI). Use of the actual ISI enables calculation of the percentage deviation in inotropy, dI [%] from normoinotropy.

When $ISI_{actual} > ISI_{ideal}$, the percentage deviation in inotropy, dI, [%], from the normoinotropy is calculated using the formula:

$$dI = +(ISI_{actual}/ISI_{ideal} - 1) \times 100 \qquad (7)$$

The sign of the deviation is positive and the deviation is expressed as XX% hyperinotropy.

When $ISI_{actual} < ISI_{ideal}$, the percentage deviation in inotropy, dI, [%], is calculated using the formula:

$$DI = -(ISI_{ideal}/ISI_{actual} - 1) \times 100 \qquad (8)$$

The sign of the deviation is negative and the deviation is expressed as XX% hypoinotropy.

Table I lists the normal values of ISI for the resting, supine adults as a function of gender. Other similarly generated tables are used to obtain values for other patients.

Utilizing the calculated dI according to Eqs.7 and 8 in conjunction with the determined $d[V \pm I]$ from Eq.6 allows separation of the effects of volume from the effects of inotropy. The percentage deviation in volemia alone, dV, [%], is then determined as the difference between the combined deviation $d[V \pm I]$ and dI using the formula:

$$dV = d[V \pm I] \pm dI \qquad (9)$$

where the true signs of individual deviations are used.

For example, if $d[V \pm I] = -39\%$ (39% hypo [volemia±inotropy]) and dI=+15% (15% hyperinotropy), then dV=−54%. Therefore, the patient is 15% hyperinotropic and 54% hypovolemic.

Determining the Deviations of Actual Vasoactivity from Normovasoactivity

Assessment of the hemodynamic modulator vasoactivity (afterload) is currently performed using Systemic Vascular Resistance Index (SVRI) [dyn.sec.cm$^{-5}$.m$^2$] as the measure of systemic vascular resistance. SVRI is calculated using the formula:

$$SVRI = 80 \, (MAP - CVP)/CI \qquad (10)$$

The deviation in systemic vascular resistance is calculated as the difference between the actual SVRI and ideal SVRI.

Using SVRI to asses vasoactivity, however, presents problems because the CI component of SVRI is a per-minute parameter which includes the chronotropic compensation of HR. See Eq.1. Since the systemic hemodynamic state responds to stimuli for every heart beat, vasoactivity (afterload) must be assessed per-beat rather than per-minute in order to correctly determine the systemic hemodynamic state. By using SVRI as the parameter of systemic vascular resistance, therefore, a clinician can completely misdiagnose an underlying hemodynamic abnormality and administer inappropriate therapy.

Therefore, according to one embodiment of the present invention, the hemodynamic assessment of vasoactivity (afterload) is performed using Stroke Systemic Vascular Resistance Index, SSVRI, a per-beat measure, in order to correctly assess vasoactivity (afterload) on a per-beat basis. SSVRI [dyn.sec.cm$^{-5}$.m$^2$] is calculated using the formula:

$$SSVRI = 80,000 \, (MAP - CVP)/ISI \qquad (11)$$

When $SSVRI_{actual} > SSVRI_{ideal}$, the percentage deviation of vasoactivity, d(Vaso), from normovasoactivity is calculated using the formula:

$$d(Vaso) = +(SSVRI_{actual}/SSVRI_{ideal} - 1) \times 100 \qquad (12)$$

The deviation is expressed as XX% vasoconstriction.

When $SSVRI_{actual} < SSVRI_{ideal}$, the percentage deviation in vasoactivity from normovasoactivity is calculated using the formula:

$$d(Vaso) = -(SSVRI_{ideal}/SSVRI_{actual} - 1) \times 100 \qquad (13)$$

The deviation is expressed as XX% vasodilation.

The disadvantages inherent in using SVRI rather than SSVRI to determine the systemic hemodynamic state can be appreciated with reference to Table II.

TABLE II

| | SI | HR | CI | MAP | CVP | SVRI | SSVRI |
|---|---|---|---|---|---|---|---|
| Adult (normal) | 47 | 72 | 3.4 | 85 | 4 | 1,930 | 137,872 |
| Adult (heart failure) | 23.5 | 144 | 3.4 | 85 | 4 | 1,930 | 275,744 |

The first row labeled "Adult (normal)" contains ideal values for hemodynamic parameters from Table I, above, including ideal values for afterload/minute (SVRI=1,930) and afterload/beat (SSVRI=137,872). The second row, labeled "Adult (heart failure)" is for a theoretical patient in heart failure in which SI is 23.5, half of the ideal value. In this patient, however, the perfusion flow CI is still 3.4, i.e. ideal, due to an appropriate chronotropic compensation, HR of 144.

If a clinician used the SVRI, the per-minute parameter of systemic vascular resistance, to assess the afterload of the patient in heart failure, the clinician would incorrectly conclude that the patient's afterload is normal (SVRI=1,930) and would not initiate vasoactive therapy. Instead, according to current protocols, the clinician would initiate empirical therapy comprising volume expansion and positive inotropic support though the patient could actually be normovolemic and normoinotropic. However, if the clinician used SSVRI, the per-beat parameter of systemic vascular resistance, to assess the patient's afterload, the clinician would correctly conclude that the cause of the patient's heart failure was due to 100% vasoconstriction (SSVRI of 275,744, twice the ideal value of 137,872) (Eq.7). The clinician would then correctly initiate afterload reduction (vasodilation) therapy.

Determining the Deviations of Actual Chronotropy from Normochronotropy

The chronotropic compensatory effect of HR is responsible for production of the perfusion-significant blood flow expressed as Cardiac Index (CI) (Eq.1). Thus, CI within the normal range shown in Table I for resting supine adults is synonymous with normochronotropy.

For $CI_{actual} > CI_{ideal}$, the percentage deviation of chronotropy, dC, [%] from normochronotropy is calculated using the formula:

$$dC = +(CI_{actual}/CI_{ideal} - 1) \times 100 \qquad (14)$$

The sign of the deviation is positive and the deviation is expressed as XX% hyperchronotropy.

For $CI_{actual} < CI_{ideal}$, the percentage deviation of chronotropy, dC, [%] from normochronotropy is calculated using the formula:

$$dC = -(CI_{ideal}/CI_{actual} - 1) \times 100 \qquad (15)$$

The sign of the deviation is negative and the deviation is expressed as XX% hyperchronotropy.

HEMODYNAMIC MANAGEMENT CHART (HMC)

The relationship between the systemic hemodynamic state (paired values of SI and MAP), and the systemic hemodynamic modulators [contractile forces (Eq.4), their deviations (Eqs.5–9), the vascular resistance forces (Eq.11) and the deviations in vasoactivity (Eqs.12–13)], produce a Hemodynamic Management Chart (HMC) when expressed graphically. The relationships expressed as a HMC are independent of whether hemodynamic data were acquired invasively, noninvasively or a combination of both.

Referring now to FIGS. 1–3, there are shown HMCs for resting, supine adults. As will be understood by those with skill in the art with reference to the disclosure herein, these HMCs are only two of an entire family of HMCs which can be constructed for the many subgroups of patients and for the many clinical states. These subgroups and clinical states include surgical patients in the immediate postoperative period, women of child bearing age and in different stages of pregnancy, neonatal, pediatric and geriatric patients, hypertensive patients and patients during physical exercise, among others. These HMCs are structured around the ideal values listed in Table I, above.

Thus, the HMC in FIG. 1 and the HMC in FIG. 2 present the relationship between the systemic hemodynamic state and the hemodynamic modulators for resting supine adults. The systemic hemodynamic state is expressed as a point shared by MAP and SI, from which can be calculated LSWI and SSVRI.

FIG. 1 presents an HMC in which hemodynamic modulators LSWI and SSVRI form the orthogonal system of coordinates and the resulting hemodynamic state, MAP and SI, are the parameters. The vertical lines are the isolines of LSWI, that is isolines of (volume±inotropy). Ideal Left Stroke Work Index ($LSWI_{ideal}$) is shown by the heavy vertical line of alternating dots and dashes labeled "0%" at LSWI=52.8. The range of normo(volemia±inotropy) is bordered by the heavy solid vertical lines at LSWI=39.3 and LSWI=73.0. The range of hypo(volemia+inotropy) is shown to the left of the heavy vertical line at LSWI=39.3. The range of hyper(volemia±inotropy) is shown to the right of the heavy vertical line at LSWI=73.0.

The horizontal lines are the isolines of SSVRI, that is isolines of vasoactivity (afterload). Normovasoactivity is shown by the heavy horizontal line of alternating dots and dashes labeled "0%" at SSVRI=137,872. The range of normovasoactivity is bordered by the heavy solid horizontal lines at SSVRI=99,692 and 185,142, and is labeled on the left border of the graph. The range of vasoconstriction is shown superior to the heavy horizontal line at SSVRI=185,142. The range of vasodilation is shown inferior to the heavy horizontal line at SSVRI=99,692.

The isolines of MAP are the diagonal lines sloping down and to the right. The normotension is shown by the downward and rightward sloping, heavy diagonal line of alternating dots and dashes at MAP=85 Torr. The normotensive range is bordered by the heavy diagonal lines at MAP=70 and 105. The range of hypertension is shown above and to the right of the heavy diagonal line at MAP=105. The range of hypotension is shown below and to the left of the heavy diagonal line at MAP=70.

The isolines of SI are the diagonal lines sloping up and to the right, perpendicular to the MAP isolines. The normodynamic state is shown by the upward and rightward sloping, heavy diagonal line of alternating dots and dashes at SI=47 ml/m$^2$. The normodynamic range is bordered by the heavy diagonal lines at SI=35 and 65. The hypodynamic range is shown above and to the left of the heavy diagonal line at SI=35. The hyperdynamic range is shown below and to the right of the heavy diagonal line at SI=65.

The hexagon shown by the very heavy solid lines delineates the loci of normal hemodynamics, that is the normal systemic hemodynamic state (normotension and normodynamic state) and normal levels of hemodynamic modulators (normo[volemia±inotropy] and normovasoactivity).

Specific therapeutic agents are available which selectively increase or decrease the levels of hemodynamic modulators, thereby allowing the clinician to alter a patient's hemodynamic state. The HMCs can be used to determine which of one or more hemodynamic modulators needs to be altered.

For example, using the HMC in FIG. 1, it can be seen that therapeutic manipulation of volume or inotropy without manipulation of vasoactivity will move the patient's hemodynamic point horizontally along the isoline of SSVRI which contains the hemodynamic point at the initiation of therapy. Volume expansion or positive inotropic therapy will move the hemodynamic point rightward causing an increase both in MAP and SI. Volume reduction, such as by diuresis, or negative inotropic therapy will move the point leftward Causing a decrease both in MAP and SI.

Similarly, therapeutic manipulation of vasoactivity will move the patient's hemodynamic point vertically along the isoline of LSWI (volume±inotropy) which contains the point at the initiation of therapy. Vasodilation will move the point down, causing a decrease in MAP and an increase in SI. Vasoconstriction will move the point up, causing an increase in MAP and a decrease in SI.

FIG. 2 presents a Hemodynamic Management Chart plotted on log/log graph paper in which MAP and SI form the orthogonal system of coordinates and hemodynamic modulators LSWI and SSVRI are the parameters. The HMC in FIG. 2 corresponds to the HMC in FIG. 1 except for the reversal of coordinates. The disclosure related to the HMC shown in FIG. 1 including the normal ranges, ideal levels and therapeutic manipulations apply to the HMC in FIG. 2 except for the differences due to the interchange of coordinates. The hemodynamic goal show in FIG. 2 is also outlined by a hexagon formed by the very heavy solid lines.

In preferred embodiments shown in FIGS. 1 and 2, the HMCs are plotted on log/log graph paper to render the nonlinear relationship between these parameters more easily discernable. However, HMCs can also be plotted on linear scale graph paper or other scale graph paper according to the present invention. FIG. 3 is an example of a plot on linear scale graph paper, but otherwise similar to the HMC in FIG. 2. FIG. 3 is plotted for ideal values of MAP=92 Torr and SI=50 ml/m$^2$. Since the values of LAP in Eq.4 and CVP in Eq. 11 are significantly smaller than the value of MAP (see Table I), the HMCs in FIGS. 1–3 plotted using an LAP of 7 Torr and a CVP of 4 Torr as constants.

HEMODYNAMIC MONITORING AND MANAGEMENT SYSTEM

According to another embodiment of the present invention, there is provided a computerized system which uses either stand-alone hemodynamic monitors connected electronically to a computer, or integrated hemodynamic monitors as components of the computer. In either case, the hemodynamic and oxygen transport data can be obtained invasively, noninvasively or by a combination of invasive or noninvasive methods.

An example of a noninvasive system uses an oscillometric sphygmomanometry to periodically monitor MAP, a TEB to continuously monitor SI, CI, HR and ISI, and pulse oximetry to continuously monitor SpO$_2$ (peripheral oxygen saturation which approximates SaO$_2$). The Hgb level is obtained through periodic blood sampling and would be entered by the operator via the computer's keyboard or other input devices such as a data line. In addition to a complete hemodynamic monitoring and management capability, this system's oxygen transport monitoring capability includes DO$_2$I.

An example of an invasive system uses an arterial line to continuously monitor MAP and to obtain samples of arterial blood. Further, a thermodilution catheter is used for periodically monitoring CI (from which SI can be calculated) and for obtaining mixed venous blood. SaO$_2$ and SvO$_2$ can then be determined from these blood samples. SvO$_2$ can also be continuously monitored invasively via an oximetric fiberoptic catheter.

According to another embodiment of the present invention, there is provided a computerized system using some invasive and some noninvasive methods according to the disclosure herein. The specific invasive and non-invasive methods selected for all systems disclosed herein will be determined by the operator according to the modalities available as would be understood by those with skill in the art with reference to the disclosure herein. Further, other invasive and non-invasive methods for obtaining hemodynamic and oxygen transport data which can be used with the systems disclosed herein will be understood by those with skill in the art.

According to another embodiment of the present invention, there is provided a computer for receiving the hemodynamic and oxygen transport data from the external or built-in monitors by a wired or-wire-less (telemetry) communication. The data can be entered automatically or manually.

In such systems disclosed herein, after the data are entered, the computer calculates LSWI (Eq.4), SSVRI (Eq.11), and the deviations in hemodynamic modulators according to the exemplary flow chart of FIG. 4. As illustrated in FIG. 4, the computer is programmed with an algorithm that includes an entry block wherein the program begins. Thereafter, the computer inputs data representing various parameters including mean blood pressure (MAP) and stroke index (SI). The computer then calculates left stroke work index (LSWI) from MAP and SI according to Eq.4. Next, the computer calculates stroke system vascular index (SSVRI) from MAP and SI according to Eq.11. The computer then calculates deviations in hemodynamic modulators d[V±I] from normovolemia/normoinotropy, in inotropy from normoinotropy, in volemia from normovolemia in vasoactivity from normovasoactivity and in chranotropy from normachranotropy according to the equations herein. The computer then branches to a selected display format which could be either a graph or tabular representation of information according to this disclosure. The program can branch to the same process or another process (not shown) or can end. The computer preferably displays both the digital values of all parameters and graphically presents their relationship to established normal ranges for the appropriated patient subgroup and clinical state. Further, the computer preferably further calculates and displays the oxygen transport parameters such as oxygen delivery index (DO$_2$I) according to Eq.2 and global oxygen consumption index (VO$_2$I) according to Eq.3 (not shown).

The computer preferably implements at least one embodiment of an HMC in its software using either a log/log scale, linear scale or other orthogonal system of coordinates, displaying one or both of the graphical (the HMC) and the quantitative information (the percentage deviations in hemodynamic state from ideal and percentage deviations in hemodynamic modulators from ideal). The computer can further plot trends of any of the processed parameters, communicate with external devices and print at least one hard copy of any data screen on the computer printer either in the digital or graphical form. Additionally, the computer can be used for teaching purposes by allowing past cases to be reviewed and by comparing patients' responses to different therapies.

Although the present invention has been described in considerable detail with reference to certain preferred embodiments, other versions are possible. For example, the invention disclosed herein can be used for mammals other than humans. Therefore, the spirit and scope of the appended claims should not be limited to the description of the preferred embodiments disclosed herein.

I claim:

1. A method of attaining a preselected combination of MAP, SI and CI in patient comprising the steps of:
    (a) determining the patient's mean arterial pressure (MAP), stroke index (SI) and cardiac index (CI);
    (b) determining the deviation from ideal of the patient's hemodynamic modulators intravascular volume, inotropy, chronotropy and vasoactivity using the MAP, SI and CI determined in step (a);
    (c) preselecting a desired combination of MAP, SI and CI; and
    (d) administering therapeutic doses of one or more pharmacologically active agents or volume expanders for altering one or more of the hemodynamic modulators to attain the preselected combination of MAP, SI and CI.

2. The method of claim 1, wherein the patient is selected from a subgroup of patients consisting of neonates, children, adult males, non-pregnant women of child bearing age, pregnant women, elderly men and elderly women.

3. The method of claim 1, wherein the one or more pharmacologically active agents or volume expanders is selected from the group consisting of a positive inotrope, a negative inotrope, a vasoconstrictor, a vasodilator, a diuretic, a positive chronotrope and a negative chronotrope.

4. The method of claim 1, wherein the preselected combination of MAP, SI and CI is a MAP between about 70–105 Torr, SI between about 35–65 ml/m$^2$ and CI between 2.8 and 4.2 l/m/m$^2$.

5. A method of attaining a preselected combination of MAP, SI and CI in patient comprising the steps of:
    (a) determining the patient's mean arterial pressure (MAP), stroke index (SI) and cardiac index (CI);
    (b) preselecting a desired combination of MAP, SI and CI; and
    (c) administering therapeutic doses of one or more pharmacologically active agents or volume expanders for altering the patient's MAP, heart rate (HR) or SI to attain the preselected combination of MAP, SI and CI.

6. The method of claim 5, wherein the patient is selected from a subgroup of patients consisting of neonates, children, adult males, non-pregnant women of child bearing age, pregnant women, elderly men and elderly women.

7. The method of claim 5, wherein the one or more pharmacologically active agents or volume expanders is selected from the group consisting of a positive inotrope, a negative inotrope, a vasoconstrictor, a vasodilator, a diuretic, a positive chronutrope and a negative chronotrope.

8. The method of claim 5, wherein the preselected combination of MAP, SI and CI is a MAP between about 70–105 Torr, SI between about 35–65 ml/m$^2$ and CI between 2.8 and 4.2 l/m/m$^2$.

9. A method of attaining a preselected combination of MAP, SI and CI, or a preselected combination of LSWI and SSVRI in patient comprising the steps of:
    (a) determining the patient's mean arterial pressure (MAP), stroke index (SI) and cardiac index (CI);
    (b) determining the patient's left stroke work index (LSWI) according to formula;

$$LSWI = A \times \{SI \times (MAP - LAP)\}$$

and determining the patient's stroke systemic vascular resistance index (SSVRI) according to the formula;

$$SSVRI = B \times (MAP - CVP)/SI$$

where LAP represents left atrial pressure, CVP represents central venous pressure and A and B are constants;
    (c) determining the patient's deviation of the combined hemodynamic modulators {volume±inotropy}, d{V±I}, from normovolemia/normoinotropy according to the formula;

$$d\{V \pm I\} = +(LSWI_{actual}/LSWI_{ideal} - 1) \times 100$$

when $LSWI_{actual} > LSWI_{ideal}$ or from the formula;

$$d\{V \pm I\} = -(LSWI_{ideal}/LSWI_{actual} - 1) \times 100$$

when $LSWI_{actual} < LSWI_{ideal}$, where $LSWI_{actual}$ is the LSWI determined in step (b) and $LSWI_{ideal}$ is known from predetermined values according to the type of patient and clinical state;
    (d) determining the patient's Inotropic State Index (ISI)
    (e) determining the patient's deviation in inotropy (dI) from normoinotropy using the formula;

$$dI = +(ISI_{ideal}/ISI_{ideal} - 1) \times 100$$

when $ISI_{actual} > ISI_{ideal}$ or from the formula;

$$dI = -(ISI_{ideal}/ISI_{actual} - 1) \times 100$$

when $ISI_{actual} < ISI_{ideal}$, where $ISI_{actual}$ is the ISI determined in step (d) and $ISI_{ideal}$ is known from predetermined values according to the type of patient and clinical state;
    (f) determining the patient's deviation in volemia, dV, from normovolenta using the formula;

$$dV = d\{V \pm I\} \pm dI$$

(g) determining the patient's deviation in vasoactivity, d(Vaso), from normovasoactivity using the formula;

$$d(Vaso) = +(SSVRI_{actual}/SSVRI_{ideal} - 1) \times 100$$

when $SSVRI_{actual} > SSVRI_{ideal}$, and from the formula;

$$d(Vaso) = -(SSVRI_{ideal}/SSVRI_{actual} - 1) \times 100$$

when $SSVRI_{actual} < SSVRI_{ideal}$, where $SSVRI_{actual}$ is the SSVRI determined in step (b) and $SSVRI_{ideal}$ is known from predetermined values according to the type of patient and clinical state;

(h) determining the patient's deviation in chronotropy (dC), from normochronotropy using the formula;

$$dC = +(CI_{actual}/CI_{ideal} - 1) \times 100$$

when $CI_{actual} > CI_{ideal}$, and from the formula;

$$dC = -(CI_{ideal}/CI_{actual} - 1) \times 100$$

when $CI_{actual} < CI_{ideal}$, where $CI_{actual}$ is the CI determined in step (a) and $CI_{ideal}$ is known from predetermined values according to the type of patient and clinical state;

(i) preselecting a desired combination of MAP, SI and CI, or a desired combination of LSWI and SSVRI; and (j) administering therapeutic doses of one or more pharmacologically active agents or volume expanders for altering one or more hemodynamic modulators to attain the preselected combination of step (i).

10. The method of claim 9, wherein the patient is selected from a subgroup of patients consisting of neonates, children, adult males, non-pregnant women of child bearing age, pregnant women, elderly men and elderly women.

11. The method or claim 9, wherein the one or more pharmacologically active agents or volume expanders is selected from the group consisting of a positive inotrope, a negative inotrope, a vasoconstrictor, a vasodilator, a diuretic, a positive chronotrope and a negative chronotrope.

12. The method of claim 9, wherein the preselected combination of MAP, SI and CI is a MAP between about 70–105 Torr, SI between about 35–65 ml/m$^2$ and CI between 2.8 and 4.2 l/m/m$^2$.

13. The method of claim 9, wherein the preselected combination of LSWI and SSVRI is a LSWI between about 39.3–73.0 g.m/m$^2$ and an SSVRI between about 99,692–185,142 dyn.sec.cm$^{-5}$.m$^2$.

* * * * *